United States Patent
McDonald et al.

(10) Patent No.: US 7,437,951 B2
(45) Date of Patent: ***Oct. 21, 2008

(54) METHOD OF USING A DIFFERENTIAL PRESSURE TYPE FLOWMETER

(75) Inventors: William G. McDonald, Scottsdale, AZ (US); David J. Monk, Mesa, AZ (US)

(73) Assignee: Freescale Semiconductor, Inc., Austin, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/842,776

(22) Filed: Aug. 21, 2007

(65) Prior Publication Data

US 2007/0277623 A1   Dec. 6, 2007

Related U.S. Application Data

(62) Division of application No. 11/324,830, filed on Jan. 3, 2006, now Pat. No. 7,261,003.

(51) Int. Cl.
G01F 1/44   (2006.01)
G01F 1/37   (2006.01)

(52) U.S. Cl. .................... 73/861.63; 73/861.52
(58) Field of Classification Search ............... 73/861.63
See application file for complete search history.

(56) References Cited

U.S. PATENT DOCUMENTS

| | | | | |
|---|---|---|---|---|
| 5,622,586 | A | | 4/1997 | Vaitkus et al. |
| 5,672,832 | A | * | 9/1997 | Cucci et al. ............... 73/861.52 |
| 5,898,108 | A | * | 4/1999 | Mieczkowski et al. ... 73/861.52 |
| 6,058,787 | A | * | 5/2000 | Hughes .................... 73/861.63 |
| 6,445,053 | B1 | | 9/2002 | Cho |
| 6,564,825 | B2 | * | 5/2003 | Lowery et al. ........... 73/861.52 |
| 6,578,435 | B2 | * | 6/2003 | Gould et al. ............. 73/861.52 |
| 6,683,370 | B1 | | 1/2004 | McDonald et al. |
| 6,813,964 | B1 | | 11/2004 | Clark et al. |
| 2006/0234414 | A1 | | 10/2006 | Van Der Wiel |

* cited by examiner

*Primary Examiner*—Harshad Patel
(74) *Attorney, Agent, or Firm*—Ingrassia, Fisher & Lorenz, P.C.

(57) ABSTRACT

A flowmeter is provided that comprises a leadframe assembly (140) and a body (144) disposed at least partially around the leadframe assembly (140). The body (144) has a flow passage therethrough that comprises a first channel (178) having a first port (166), a second channel (180) having a second port (168), and a flow altering element (182) disposed within the second channel (180). First and second pressure sensors (174 and 176) are disposed within the body (144) and coupled to the leadframe assembly (140) for measuring a first pressure within the first channel (178) and a second pressure within the second channel (180), respectively. An integrated circuit (155), which is coupled to the leadframe assembly (140), to the first pressure sensor (174), and to the second pressure sensor (176), is configured to determine the rate of flow through the flow passage from the first pressure and the second pressure.

10 Claims, 4 Drawing Sheets

METHOD OF USING A DIFFERENTIAL PRESSURE TYPE FLOWMETER

CROSS-REFERENCE TO RELATED APPLICATIONS

This application is a divisional of patent application Ser. No. 11/324,830, filed Jan. 3, 2006, now U.S Pat. No. 7,261,003.

FIELD OF THE INVENTION

This invention generally relates to a flowmeter and, more particularly, to a small scale fluid flow sensor assembly that is manufactured utilizing conventional component-level packaging and high volume manufacturing techniques and a method for the production thereof.

BACKGROUND OF THE INVENTION

Small scale fluid flow sensor assemblies are currently employed in a wide variety of applications ranging from industrial fluid flow applications to medical therapy delivery devices. For example, such sensor assemblies may be utilized in conjunction with intravenous (IV) fluid delivery devices to monitor flow characteristics of an IV solution to a patient. Additionally, such sensor assemblies may be utilized in conjunction with certain respiratory equipment. This notwithstanding, the manufacture of such fluid flow measurement sensor assemblies typically involves significant production costs due to the use of unique and customized fabrication processes. These costs are especially significant in applications in which the fluid flow measurement sensor assemblies are routinely discarded; e.g., when such sensor assemblies are used in disposable devices, such as IV fluid delivery devices of the type mentioned above.

One known type of fluid flow measurement sensor assembly that may be somewhat less costly to produce comprises a longitudinal housing that defines a cavity and a fluid flowbody having a flow restricting element therein (e.g., a constriction, such as a venturi). The cavity is disposed at an intermediate portion in the housing and includes (1) a relatively large chamber accessible at an outer surface of the housing, (2) a first aperture that joins the chamber to the flowbody proximate an upstream portion thereof, and (3) a second aperture that joins the chamber to the flowbody proximate a downstream portion thereof. A fluid flow measurement device is disposed within the chamber. The device includes first and second conventional fluid pressure probes or sensors (e.g., micro-electromechanical system, or MEMS), which are disposed in the upstream aperture and the downstream apertures, respectively. As a fluid (e.g., a liquid) passes through the flowbody, the sensors measure the pressure of the fluid at the upstream and downstream portions of the constriction, and the fluid flow measurement device determines the rate of fluid flow.

Though fluid flow sensor assemblies of the type described above may be somewhat less costly to produce than other known sensor assemblies, the production of these sensor assemblies still requires a unique and customized fabrication process, particularly in the manufacture of the flowbody housing, and is thus still relatively expensive. Considering this, it should be appreciated that it would be desirable to provide a fluid flow sensor assembly that is less costly to produce by, for example, utilizing conventional component-level packaging and high volume manufacturing techniques. Additionally, it should be appreciated that it would be desirable to provide a method for the producing such a fluid flow sensor assembly. Furthermore, other desirable features and characteristics of the present invention will become apparent from the subsequent detailed description of the invention and the appended claims, taken in conjunction with the accompanying drawings and this background of the invention.

BRIEF DESCRIPTION OF DRAWINGS

The preferred exemplary embodiment of the present invention will hereinafter be described in conjunction with the appended drawings, where like designations denote like elements, and.

DETAILED DESCRIPTION OF THE INVENTION

The following detailed description of the invention is merely exemplary in nature and is not intended to limit the invention or the application and uses of the invention. Furthermore, there is no intention to be bound by any theory presented in the preceding background of the invention or the following detailed description of the invention.

Figure 1:
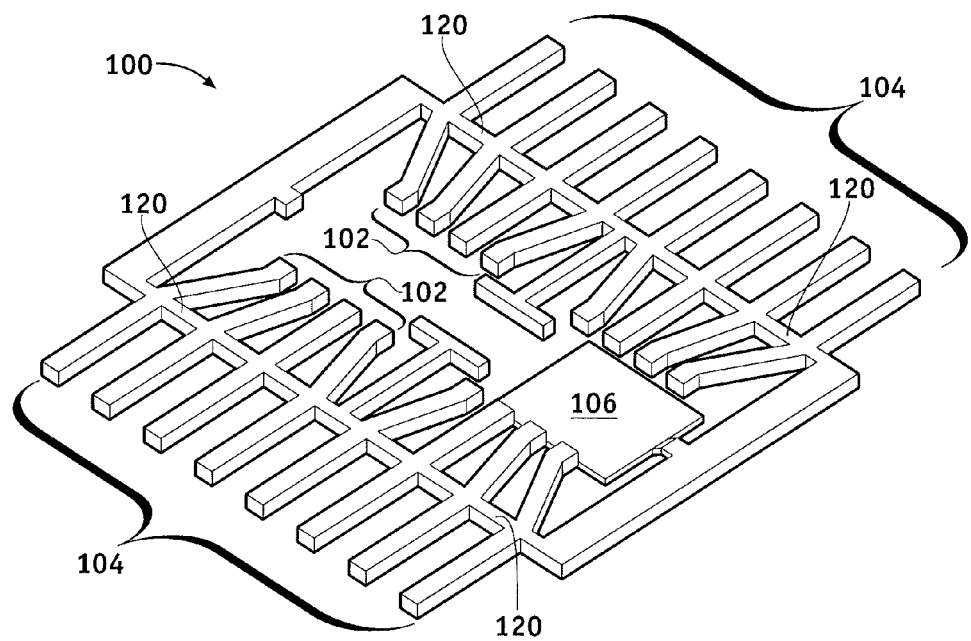
FIG. 1 is an isometric view of a known leadframe suitable for use in conjunction with the present invention.
Figure 2:
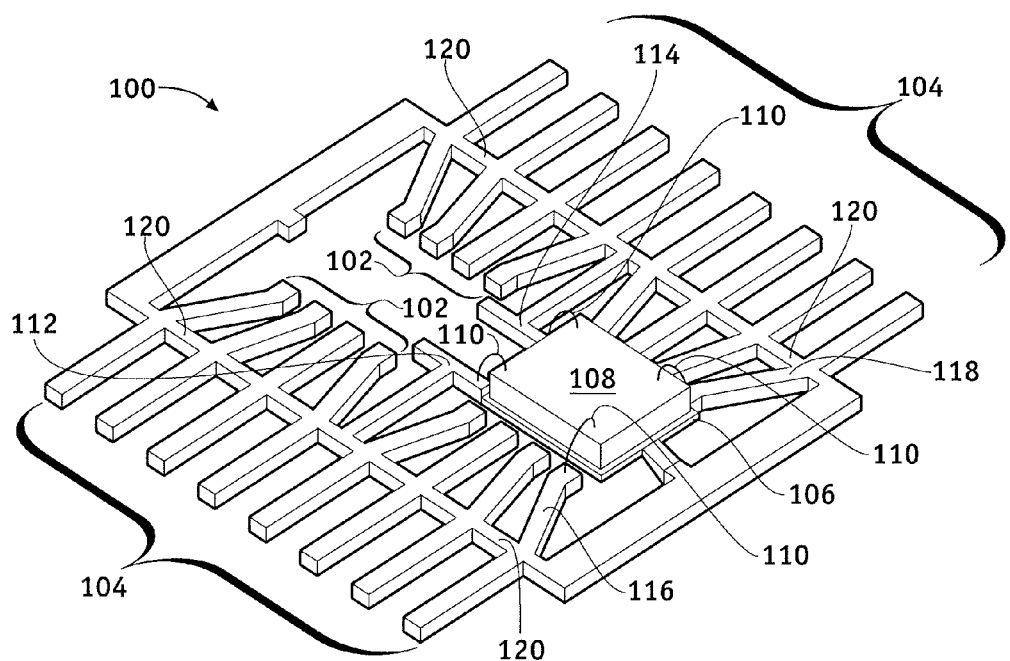
FIG. 2 is an isometric view of the leadframe shown in FIG. 1 having an integrated circuit (IC) device mounted thereon.

FIGS. 1 and 2 are isometric views of an exemplary leadframe 100 upon which the remainder of the inventive flowmeter is assembled. Leadframe 100 is produced by known means; e.g., by stamping a portion of a metal (e.g., copper or copper alloy) strip with a predetermined pattern of leadframe features (e.g., die attach flags, interior electrical contacts, exterior electrical contacts, etc.). In this particular case, leadframe 100 comprises a plurality of interior electrical contacts 102, a plurality of exterior electrical contacts 104, and a die attach flag 106. As shown in FIG. 2, die attach flag 106 is configured to support an integrated circuit (IC) die or device 108, such as an application specific integrated circuit (ASIC). Conventional die bonding is utilized to secure IC device 108 to die attach flag 106 with a suitable bonding material (e.g., epoxy, glass, gold preform, solder paste, etc.). After being secured to flag 106, device 108 is wire bonded to a selected group of interior electrical contacts 102 with, for example, segments of gold wire as shown in FIG. 2 at 110. As illustrated in FIG. 2, for example, leadframe 100 may be wire bonded to first and second interior-to-interior electrical connections 112 and 114, and to first and second interior-to-exterior electrical connection 116 and 118. A dam bar 120 is provided around the perimeter of leadframe 100; however, it should be understood that dam bar 120 is later removed (i.e., trimmed) from leadframe 100 during device processing to physically separate and electrically isolate adjacent ones of contacts 102 and 104.

After IC device 108 has been die bonded to flag 106 and wire bonded to selected ones of interior electrical contacts 102, a portion of leadframe 100 may be overmolded with a composite material (e.g., plastic) to create a molded body. If desired, IC device 108 may be entirely encapsulated within the molded body to provide environmental protection and to prevent wire bond corrosion. Alternatively, a cavity may be formed around IC device 108 to permit access to device 108. This cavity may later be partially or fully filled with a suitable sealant (e.g., a potting gel) or simply covered by attaching a protective cover to the molded body.

Figure 3:
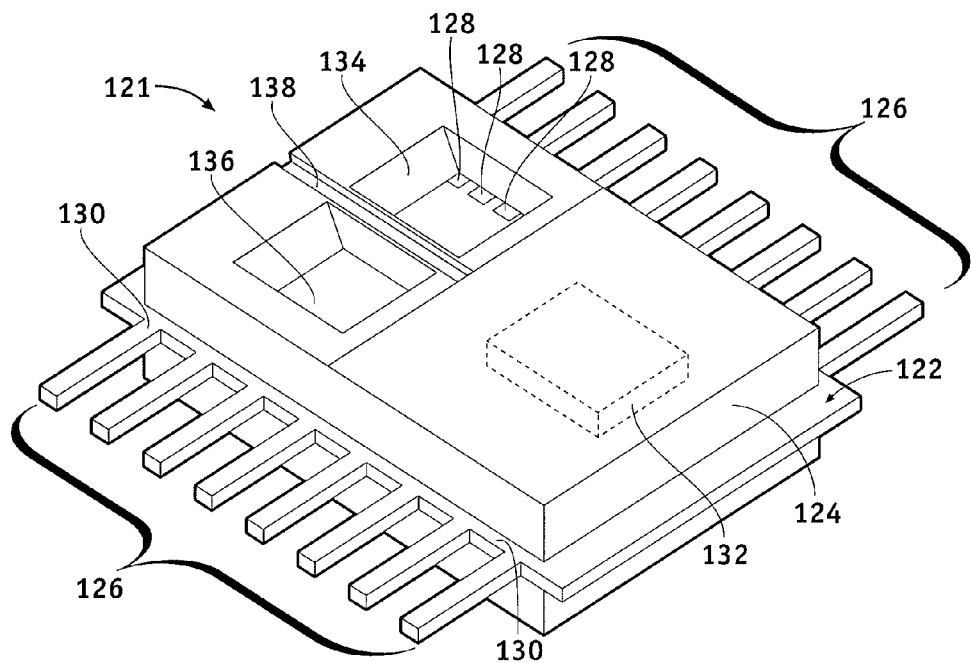
FIGS. 3 and 4 are isometric views of an overmolded device including the leadframe shown in FIG. 1 in accordance with first and second embodiments of the present invention, respectively.

FIG. 3 illustrates an overmolded leadframe assembly 121 comprising a leadframe 122 and an IC device 132 coupled thereto, which is shown in phantom in FIG. 3. As described above in conjunction with FIGS. 1 and 2, leadframe 122 includes a plurality of exterior electrical contacts 126, a plurality of interior electrical contacts 128, and a dam bar 130. As can be seen, a molded (e.g., plastic) body 124 has been formed around leadframe 122 that includes a first cavity 134 and a second cavity 136. Cavities 134 and 136 are provided through an upper surface of body 124 and each extend downward therefrom to expose a portion of leadframe 122 and at least one of interior electrical contacts 128. IC device 132, which is encapsulated within body 124 substantially adjacent cavities 134 and 136, is wire bonded to the exposed interior electrical contacts. Thus, IC device 132 may electrically communicate with other devices that are disposed within cavities 134 and 136 and likewise coupled to the exposed contacts. In particular, IC device 132 may communicate with first and second pressure sensors disposed within cavities 134 and 136, respectively, as will be described in more detail below.

Still referring to FIG. 3, a depression (e.g., an elongated groove) 138 may also be provided in an upper surface of molded body 124. As will be seen, depression 138 is configured to receive therein a conforming raised portion (e.g., a longitudinal ridge) provided on a ported cover member that is to be secured to body 124. When the ported cover member is placed in an abutting relationship with the upper surface of body 124, the raised portion may fit into depression 138 and thus provide alignment and stability to the resulting body/cover member assembly. This notwithstanding, it should be appreciated that the provision of a depression, depressions, or other alignment means on the surface of body 124 is merely optional and is by no means required to implement the inventive flowmeter.

Figure 4:
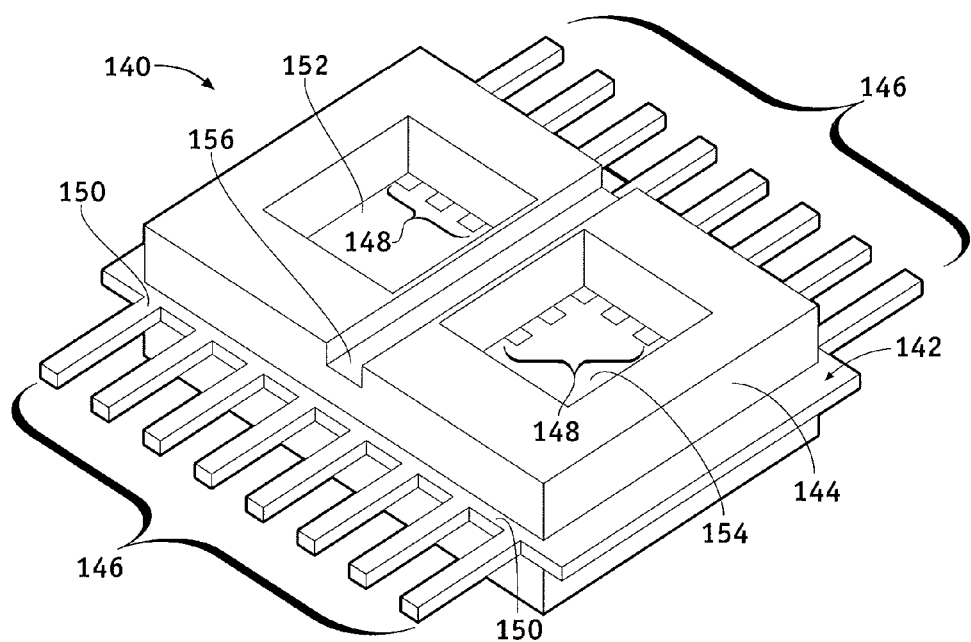

FIG. 4 illustrates an overmolded leadframe assembly 140 including a leadframe 142 comprising a plurality of exterior electrical contacts 146, a plurality of interior electrical contacts 148, and a dam bar 150. Leadframe 142 has been overmolded in accordance with a second embodiment of the present invention to create a molded body 144 having a first cavity 152, a second cavity 154, and an elongated groove 156 in an upper surface thereof. As was the case previously, an IC device 155 (shown in FIG. 7 discussed below) is disposed within assembly 140 and coupled to leadframe 142; however, in contrast to IC device 132 of assembly 121 shown in FIG. 3, IC device 155 is disposed within a lower region of molded body 144 substantially opposite the upper surface thereof (i.e., IC device 155 is bonded to the underside of leadframe 142) and is thus hidden from view in FIG. 4. As may be appreciated by comparing FIGS. 3 and 4, this configuration allows cavities 152 and 154 to be made substantially larger than cavities 134 and 136, which may facilitate the insertion of pressure sensors into cavities 152 and 154 and the wire bonding of such pressure sensors to interior contacts 148 as further described below.

Figure 5:
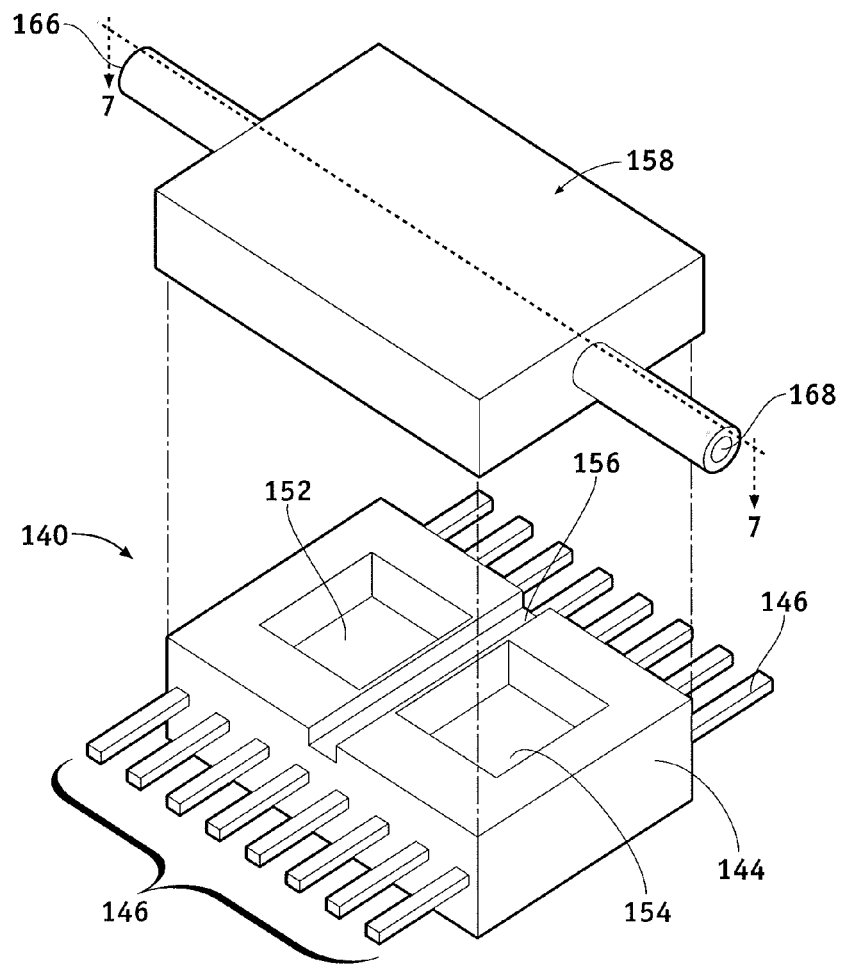
FIG. 5 is an isometric view of the overmolded leadframe shown in FIG. 4 and a ported cover member.
Figure 6:
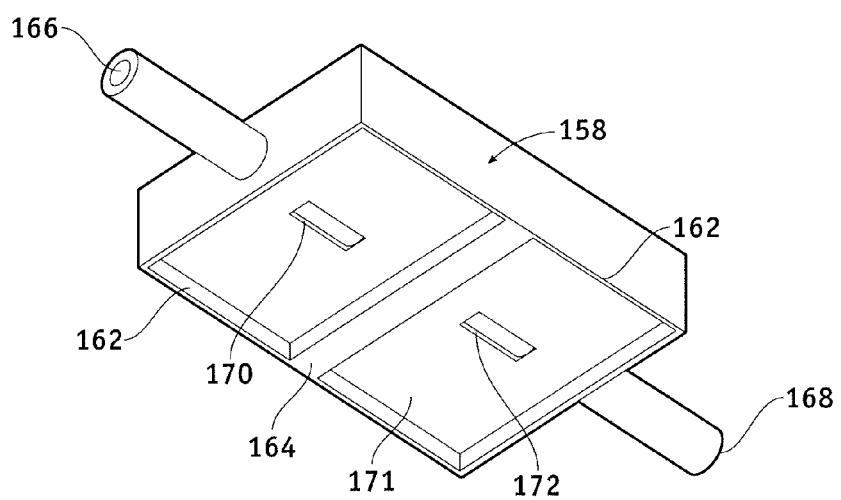
FIG. 6 is an isometric view of the underside of the ported cover member shown in FIG. 5.

FIG. 5 is an isometric view of a ported cover member 158 that is configured to abuttingly engage and be secured to overmolded leadframe assembly 140 creating an air tight seal by, for example, sonic welding or application of an adhesive bonding material. In particular and as illustrated in FIG. 6 (an isometric view of the underside of cover member 158), a peripheral skirt 162 is disposed around cover member 158 and configured to extend over and around the upper edge of body 144 when cover member 158 is secured to body 144. A medial ridge 164, which generally conforms to groove 156 disposed on body 144, may also be provided on the underside of cover member 158. When cover member 158 is secured to body 144, medial ridge 164 is received within groove 156 to provide added alignment and stability. For the sake of completeness, it should be noted that, before or after cover member 158 is affixed to overmolded leadframe assembly 144, several additional processing steps may be performed, such as: (1) a curing step wherein body 144 and cover member 158 are baked to harden and strengthen the durability of their plastic molded bodies; (2) a labeling step wherein the flowmeter is marked for identification purposes; (3) a trimming step wherein dam bar 150 is removed along with any excess mold flashes; and (4) a singulation step wherein leadframe 142 (FIG. 4), and thus overmolded leadframe assembly 140, is separated from adjoining leadframes. Lastly, to complete manufacture, the flowmeter may be plated (e.g., with lead and tin), inspected, and shipped.

Cover member 158 is configured to conduct a fluid (e.g., a liquid) from inlet port 166 to outlet port 168. In addition, cover member 158 is configured to direct fluid flow over cavities 152 and 154 provided within molded body 144. To accomplish this, an upstream opening 170 and a downstream opening 172 are provided through a lower surface 171 of cover member 158 (FIG. 6). When cover member 158 is secured to body 144, fluid (1) enters inlet port 166, (2) flows over upstream opening 170 and cavity 152, (3) flows over downstream opening 172 and cavity 154, and (4) exits outlet port 168. As will be more fully described below, the upstream and downstream pressures exerted by the flowing fluid may be measured by first and second pressure sensors, which are disposed within cavities 152 and 154.

Figure 7:
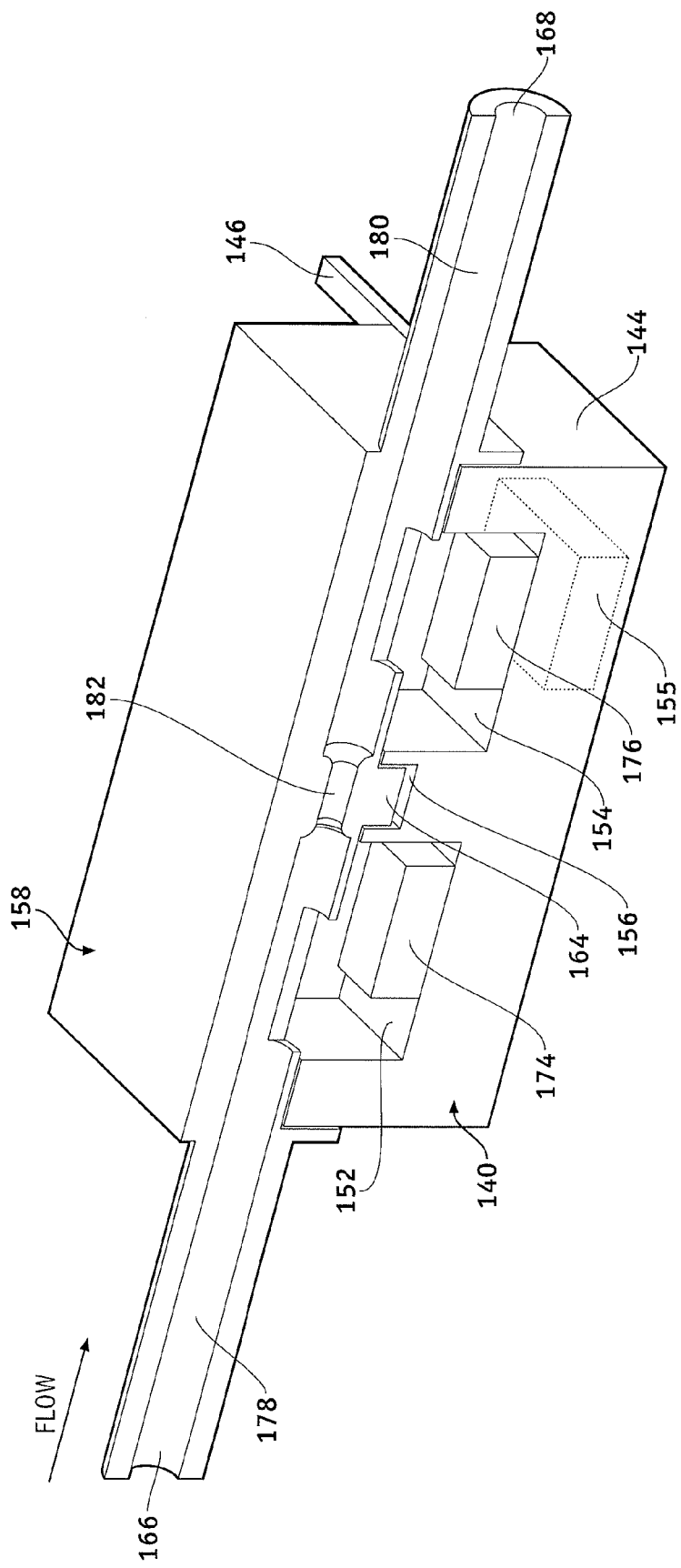
FIG. 7 is a cross-sectional view of the overmolded leadframe shown in FIG. 5 taken along line 7-7 having the ported cover member coupled thereto.

FIG. 7 is a cross-sectional view of the device shown in FIG. 5 taken along line 7-7 after ported cover member 158 has been secured to overmolded leadframe assembly 140. In this view, it may be appreciated that first and second pressure sensors 174 and 176 have been disposed within cavities 152 and 154, respectively. After insertion into the cavities, pressure sensors 174 and 176 are each wire bonded to interior electrical contacts 148 (FIG. 4). If desired, a suitable gel (e.g., a potting gel) may be deposited into cavities 152 and 154 to protect sensors 174 and 176, respectively, from corrosion and to isolate the wire bonds.

Referring still to FIG. 7, ported cover member 158 includes a flow passage having an inlet channel 178 and an outlet channel 180. In accordance with the present invention, a flow altering element is disposed within the flow passage (e.g., within inlet channel 178, within outlet channel 180, or between channels 178 and 180) to alter the rate of fluid flow therethrough. It is preferable that the element takes the form of a flow restricting element, such as flow restricting element 182 shown in FIG. 7. As can be seen in FIG. 7, flow restricting element 182 may be provided within cover member 158 intermediate channels 178 and 180 and may comprise a flow passage having a reduced inner diameter (e.g., a constriction, such as venturi); however, it should be appreciated that flow restricting element 182 may take other forms that are capable of impeding fluid flow (e.g., an orifice plate, a baffle extending into the flow passage, etc.). Due to the presence of flow restricting element 182, the pressure of the fluid flowing through the flow passage provided within ported cover member 158 will be greater within inlet channel 178 than within outlet channel 180. More specifically, when fluid flows from inlet channel 178 through flow restricting element 182 to outlet channel 180, the rate of fluid flow will increase, the pressure exerted by the fluid will decrease, and a partial vacuum will be created in accordance with the Bernoulli effect. This change in pressure may be measured by sensors 174 and 176 and utilized by IC device 155 to determine the rate of fluid flow as described below.

Cover member 158 may be manufactured utilizing known molding techniques, such as those utilized to form molded body 118. One or more pins may be inserted into a cast of cover member 158 during molding to form a longitudinal cavity that comprises the flow passage. For example, to form the flow passage shown in FIG. 7, first and second pins may be inserted into the cover member cast at locations corresponding to inlet port 166 and outlet port 168, respectively. The body of the first pin may define inlet channel 178, and the body of the second pin may define outlet channel 180. Additionally, the pins may each have a tapered distal end that defines a portion of flow restricting element 182. During the molding process, a molding material is introduced into the cover member cast and allowed to form around the pins. After the mold has set, the first and second pins are extracted from the cast thus creating inlet channel 178, outlet channel 180, and flow restricting element 182.

As flow restricting element 182 impedes the flow of fluid through ported cover member 158, a pressure differential is created between inlet channel 178 and outlet channel 180 and, therefore, between cavity 152 and cavity 154. As previously described, channels 178 and 180 are configured to fluidly communicate with cavities 152 and cavities 154, respectively. Pressure sensor 174 measures an upstream pressure within cavity 152, while pressure sensor 176 measures a downstream pressure within cavity 154. Sensors 174 and 176 relate the measured pressures to IC device 155 contained within overmolded leadframe assembly 140, which then determines the pressure differential between the two cavities and, subsequently, the rate of fluid flow. Sensors 174 and 176 are preferably absolute pressure sensors and may comprise piezoresistive-transducer (PRT) type sensors, micro-machined-electro-mechanical-system (MEMS) type sensors, or the like. As such sensors are well-known in the art, further discussion of sensors 174 and 176 is not deemed necessary at this time; however, the interested reader is referred to U.S. Pat. No. 4,347,745 entitled "Pressure Measuring Apparatus" issued Sep. 7, 1982, and to U.S. Pat. No. 6,445,053 entitled "Micro-Machined Absolute Pressure Sensor" issued Sep. 3, 2002.

It should be appreciated from the above that a flowmeter has been provided, which may be produced utilizing conventional component-level packaging and high volume manufacturing techniques. If should further be appreciated that a method for producing such a flowmeter has also been provided. In an exemplary embodiment, the flowmeter comprises a leadframe assembly and a body disposed at least partially around the leadframe assembly. The body has a flow passage therethrough that comprises a first channel having a first port, a second channel having a second port, and a flow altering element disposed within the second channel. First and second pressure sensors are disposed within the body and coupled to the leadframe assembly for measuring a first pressure within the first channel and a second pressure within the second channel, respectively. An integrated circuit, which is coupled to the leadframe assembly, to the first pressure sensor, and to the second pressure sensor, is configured to determine the rate of flow through the flow passage from the first pressure and the second pressure.

If desired, the flow alerting element may comprise a region within the second channel having a reduced diameter, which may be, for example, a venturi. The body may comprise a leadframe body and a cover member that is fixedly coupled to the body and cooperates therewith to form the flow passage. The leadframe body may include an upper surface, and the cover member may include a lower surface configured to abuttingly engage the upper surface. A skirt may be provided on the lower surface and configured to extend around the perimeter of the upper surface when the cover member is fixedly to the leadframe body. Also, the lower surface may include a raised portion, and the upper surface may include a depression therein. The raised portion is configured to be received by the depression when the cover member is fixedly coupled to the leadframe body.

Furthermore, the body may comprise an upper surface, a first cavity disposed within the body and through the upper surface for receiving the first pressure sensor, and a second cavity disposed within the body and through the upper surface for receiving the second pressure sensor. The cover member may comprise: (1) a first aperture extending from the lower surface to the first channel for permitting fluid communication between the first channel and the first cavity when the cover member is fixedly coupled to the leadframe body, and (2) a second aperture extending the from lower surface to the second channel for permitting fluid communication between the second channel and the second cavity when the cover member is fixedly coupled to the leadframe body. Additionally, the integrated circuit may be disposed within the leadframe body substantially adjacent to the first and the second cavities. Alternatively, the leadframe body may include a lower portion substantially opposite the upper surface and the integrated circuit may be disposed therein. Lastly, the first and the second pressure sensors may be absolute pressure sensors.

In a further exemplary embodiment, the flowmeter comprises a leadframe assembly and a body disposed at least partially around the leadframe assembly. The body has first and second cavities therein. A cover member, which is fixedly coupled to the body so as to enclose the first and second cavities, has a fluid passage therethrough that comprises an upstream channel having an inlet port, a downstream channel having an outlet port, and a flow restricting element disposed within the downstream channel. A first pressure sensor, which is disposed within the first cavity and coupled to the leadframe assembly, is configured to measure an upstream pressure within the upstream channel. Similarly, a second pressure sensor, which is disposed within the second cavity and coupled to the leadframe assembly, is configured to measure a downstream pressure within the downstream channel. An integrated circuit is disposed within the body and coupled to the leadframe assembly, to the first pressure sensor, and to the second pressure sensor. The integrated circuit is configured to determine the rate of flow through the flow passage from the upstream pressure and the downstream pressure.

The flowmeter's cover member may comprise a lower surface and first and second apertures. The first aperture extends from the lower surface to the upstream channel for permitting fluid communication with the first cavity when the cover member is coupled to the body, and the second aperture extends the from lower surface to the downstream channel for permitting fluid communication with the second cavity when the cover member is coupled to the body. If desired, the lower surface may include a raised portion, and the body may include a depression for receiving the raised portion. In particular, the raised portion may comprise a longitudinal ridge between the first and the second apertures, and the depression may comprise a longitudinal groove between the first and the second cavities. In addition, the leadframe body may include a lower portion that is substantially opposite the upper surface and that houses the integrated circuit. Finally, the first and the second pressure sensors may be absolute pressure sensors.

In yet a further exemplary embodiment, a method for producing a flowmeter is provided wherein a molded body, which has first and second cavities provided through a first surface thereof, is formed at least partially around a leadframe assembly including a leadframe and an integrated circuit device bonded thereto. First and second pressure sensors are disposed into the first and second cavities, respectively, and coupled to the integrated circuit device. A cover member is coupled at a second surface thereof to the first surface of the molded body. The cover member includes a flow passage having an inlet, an outlet, a flow restricting element disposed between the inlet the outlet, and first and second apertures through an upstream portion and a downstream portion of the flow passage for permitting fluid communication with the first and second pressure sensors, respectively. Additionally, a molding material may be dispensed into a cast to produce the cover member, and at least one pine may be inserted into and withdrawn from the cast to produce at least a portion of the flow passage.

Although discussed above in conjunction with an exemplary leadframe packaging, it should be appreciated that the inventive flowmeter may be used in conjunction with a variety of leadframe packages including quad flat non-leaded packages. The embodiments and examples set forth herein were presented in order to best explain the present invention and its particular application and to thereby enable those skilled in the art to make and use the invention. However, those skilled in the art will recognize that the foregoing description and examples have been presented for the purposes of illustration and example only. The description as set forth is not intended to be exhaustive or to limit the invention to the precise form disclosed. Many modifications and variations are possible in light of the above teaching without departing from the spirit of the forthcoming claims.

The invention claimed is:

1. A method for measuring the rate of fluid flow in a flow passage, comprising the steps of:
    providing a molded body formed at least partially around a leadframe assembly and having a flow passage therethrough;
    measuring a first pressure of the fluid in a first channel within the flow passage;
    altering the flow in a second channel within the flow passage;
    measuring a second pressure of the fluid in the second channel;
    determining the rate of fluid flow based on the first pressure and the second pressure.

2. The method of claim 1, wherein altering the flow includes providing a region within the second channel having a reduced diameter.

3. The method of claim 2, wherein altering the flow includes providing a venturi region.

4. The method of claim 1, wherein the determining step includes using an integrated circuit to determine the rate of fluid flow.

5. The method of claim 1, wherein the measuring steps include measuring an absolute pressure of the fluid.

6. A method for measuring flow, comprising the steps of:
    providing a molded body at least partially around a leadframe assembly including a leadframe and an integrated circuit device bonded thereto, such that the molded body has first and second cavities provided through a first surface thereof, providing first and second pressure sensors within the first and second cavities, respectively, and coupling the first and second pressure sensors to the integrated circuit device; and
    providing a cover member coupled at a second surface thereof to the first surface of the molded body, the cover member including a flow passage having an inlet, an outlet, and first and second apertures through an upstream portion and a downstream portion of the flow passage for permitting fluid communication with the first and second pressure sensors, respectively;
    providing a flow restricting element disposed between the inlet and the outlet;
    measuring, using the first pressure sensor, a first pressure of the fluid in the first cavity;
    measuring, using the second pressure sensor, a second pressure of the fluid in the second cavity; and
    determining, using the integrated circuit, the rate of fluid flow based on the first pressure and the second pressure.

7. The method of claim 6, wherein providing a flow restricting element includes providing an element having a reduced diameter relative to the first and second apertures.

8. The method of claim 7, wherein providing a flow restricting element includes providing a venturi element.

9. The method of claim 7, wherein the measuring steps include measuring an absolute pressure of the fluid.

10. The method of claim 6, wherein said first surface includes a skirt portion configured to extend around the perimeter of said second surface when said cover member is fixedly coupled to said leadframe body.

* * * * *